United States Patent [19]
Chizhov et al.

[11] Patent Number: 5,658,886
[45] Date of Patent: Aug. 19, 1997

[54] **ACRIDINONE DERIVATIVE, COMPOSITIONS CONTAINING SAME AND A METHOD FOR USING SAME TO TREAT *CHLAMYDIA TRACHOMATIS***

[75] Inventors: Novomir Pavlovich Chizhov; Roald Antonovich Kupchinsky; Ljudmila Evgenievna Alekseeva; Aleksei Leonidovich Kovalenko; Margarita Alekseevna Borisova, all of St.-Petersburg, Russian Federation

[73] Assignee: Limited Liability Partnership "POLYSAN", St-Petersburg, Russian Federation

[21] Appl. No.: 351,385

[22] PCT Filed: Feb. 23, 1994

[86] PCT No.: PCT/RU94/00032

§ 371 Date: Dec. 7, 1994

§ 102(e) Date: Dec. 7, 1994

[87] PCT Pub. No.: WO94/22837

PCT Pub. Date: Oct. 13, 1994

[30] Foreign Application Priority Data

Apr. 1, 1993 [RU] Russian Federation ............ 93017260

[51] Int. Cl.$^6$ ............................................................ A61K 31/70
[52] U.S. Cl. ............................. 514/25; 514/297; 514/931; 536/4.1; 546/103
[58] Field of Search ............................. 514/25, 297, 931; 546/103; 536/4.1

[56] References Cited

U.S. PATENT DOCUMENTS

| 3,681,360 | 8/1972 | Fryer . |
| 4,244,954 | 1/1981 | Schulenberg . |
| 4,362,720 | 12/1982 | Lemieux . |
| 4,366,318 | 12/1982 | Cain . |
| 4,399,283 | 8/1983 | Fisher . |
| 4,711,889 | 12/1987 | Brombacher . |
| 5,175,172 | 12/1992 | Dietlin . |

FOREIGN PATENT DOCUMENTS

| 098 098 A2 | 1/1984 | European Pat. Off. . |
| 110 298 B1 | 6/1984 | European Pat. Off. . |
| 375 471 A2 | 6/1990 | European Pat. Off. . |
| 494 623 A1 | 7/1992 | European Pat. Off. . |
| 2759468 | 6/1979 | Germany . |
| 63-310826 | 12/1988 | Japan . |
| 64-40426 | 2/1989 | Japan . |
| 139 805 | 7/1987 | Poland . |
| WO91/02725 | 3/1991 | WIPO . |
| WO92/16509 | 10/1992 | WIPO . |

OTHER PUBLICATIONS

Chizhov et al., Section 5.2 "Low–Molecular Interferon Inductors" in *Principles of Experimental Chemotherapy for Viral Infections*, Riga, 82 (1988).

Chizhov, "Chemotherapy for Aids: Outcome and Promise," *Antibioki i Khimioterapiia*, 38(4): 38–41 (1991).

Denny et al., "Potential Antitumor Agents. 49. 5–Substituted Derivatives of N–[2–(Dimethylamino) ethyl]–9–aminoacridine–4 –carboxamide with in vivo Solid Tumor Activity," *J. Med. Chem.*, 30(4): 658–663 (1987).

Mashkovskii, Section 5 "Oletetrinum" in *Medistina*, Part 2: 221 (1987).

Modianova, "Cell Cohesion in Lung Tissue of Mice Lines and their Sensitivity to Lung Tumor Induction with Ethyl Carbonate (Urethane)," *Voprosy Onkologii*, 19(6): 83–88 (1973).

Modianova, "Cellular Cohesive Force in the Pulmonary Tissue of Mice of Different lines and Their Sensitivity to Induction of Pulmonary Tumors by Urethan," *Problemy Experimental'nojo Kantscrogeneza*, 51: 135–139 (1983).

Palmer et al., "Potential Antitumor Agents. 54. Chromophore Requirements for in vivo Antitumor Activity among the General Class of Linear Tricyclic Carboxamides," *J. Med. Chem.*, 31: 707–712 (1988).

Smorodintsev et al., "Acarid–Bite Encephalitis and Related preventive Vaccination" (1986).

*Primary Examiner*—James O. Wilson
*Attorney, Agent, or Firm*—Marshall, O'Toole, Gerstein, Murray & Borun

[57] ABSTRACT

The claims cover a bioactive compound N-methyl-N-α-D-glucopyranosil-ammonium-2-acridone-9-on-10-yl-acetate designated CYCLOFERONE which was obtained by chemical synthesis and is a heterocyclic compound. Specifically CYCLOFERONE is an acridanone derivative of formula

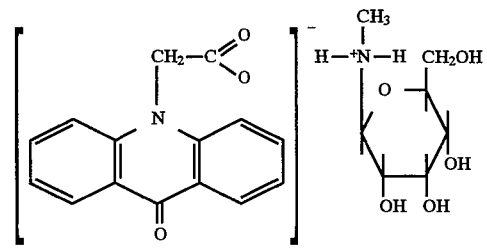

CYCLOFERONE exhibits interferonogenic, anti-vital (including anti-HIV), anti-parasitic, anti-promotive, and radioprotective effects.

3 Claims, No Drawings

ACRIDINONE DERIVATIVE, COMPOSITIONS CONTAINING SAME AND A METHOD FOR USING SAME TO TREAT *CHLAMYDIA TRACHOMATIS*

TECHNICAL FIELD

The invention relates to medicinally useful bioactive substances manufactured by chemical techniques. Particularly, the invention relates to new derivatives of acridanones having the general formula /1/

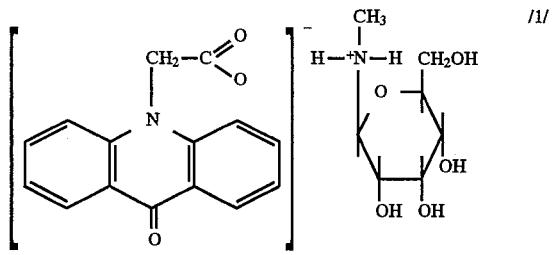

which possess a wide range of bioactivities such as interferonogenic, anti-viral (including anti-HIV), anti-parasitic, anti-promotive, and radioprotective activities.

BACKGROUND OF THE INVENTION

Compounds of acridanone class occur in nature and acridanone derivatives have been synthesized by chemical means. Acridanone derivatives have been reported to have anti-tumor and anti-viral activities. See Japanese Published Patent Application Nos. 64–40426 of Feb. 10, 1989 and 63-310826 of Dec. 19, 1988. Naturally occurring compounds of the same class have been described as having anti-protozoal and anti-herpetic activities. See U.S. Pat. No. 4,244,954 of Jan. 13, 1978 and European Publication No. 110 298 of Jun. 13, 1984.

A structural analog of the acridanone cycloferone, namely 10-carboxymethyl-9-acridone dimethyl-aminoethylether chlorhydrate, of the general formula /2/

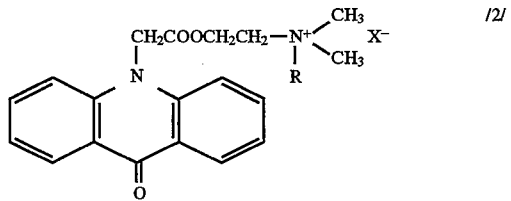

(where R is hydrogen) has been reported to have interferonogenic activity. The analog is distinguished from cycloferone by a substitution in position 10 of the acridone cycle. See Polish Patent 139 805 of Jul. 31, 1984. The cycloferone analog exhibits lower interferonogenic activity when compared to the compound of the present invention and exhibits the same level of toxicity.

SUMMARY OF THE INVENTION

The goal of the invention was to obtain a new acridanone derivative possessing a wide range of biological activities, low toxicity, and superior chemotherapeutic properties.

The goal was accomplished in the synthesis of compounds of general formula /1/, obtained through the interaction of the compound of general formula /3/

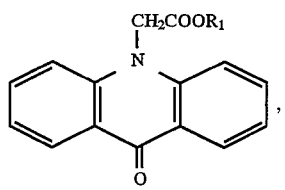

(where $R_1$ is a hydrogen, alkyl group, metal or ammonium cation) with derivatives of L,D-glucopyranosilamine of general formula /4/

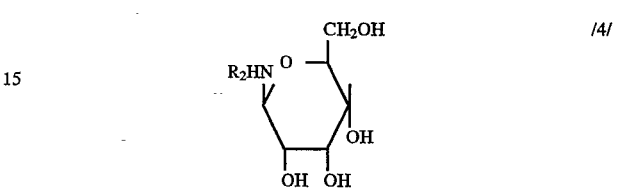

(where $R_2$ is a methyl group).

The presently preferred derivative is N-methyl-N-α-D-glucopyranosil-ammonium-2-acridone-9-on-10-yl-acetate, having the formula

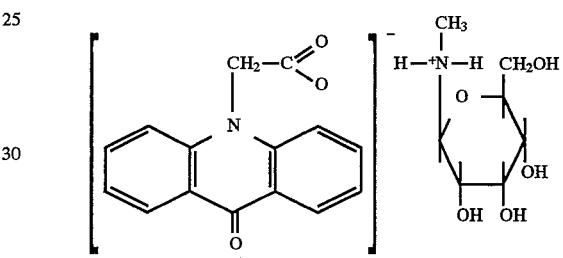

The derivative has interferonogenic, anti-viral (including anti-HIV), anti-parasitic, anti-promotive, and radioprotective activities and is designated CYCLOFERONE herein. The name CYCLOFERONE has been registered as a trademark in Russia.

Due to its low toxicity, it is contemplated that CYCLOFERONE (N-methyl-N-α-D-glucopyranosil-ammonium-2-acridone-9-on-10-yl-acetate) be formulated as a medication for parenteral, oral, and topical application.

DETAILED DESCRIPTION

Example 1

Preparation of CYCLOFERONE

Case 1 99.6 grams of N-methyl-N-α,D-glucopyranosilamine was dissolved in 200 milliliters of distilled water. Then, gradually, 125 grams of carefully fragmented 2-/acridone-9-on-10-yl/acetic acid was added with stirring. Stirring continued at room temperature until solids were completely dissolved, and then 1 liter of ethyl alcohol was added. The resulting precipitate was filtered, washed in 100 ml ethyl alcohol, re-filtered, and dried for 1 hour at 60° C. 224 grams of 100% pure N-methyl-N-α-D-glucopyranosil-ammonium-2-acridone-9-on-10-yl-acetate (CYCLOFERONE) of formula $C_{22}H_{26}N_2O_8$ were thus obtained in yellow crystals upon re-crystallization using low-grade alcohols. The melting point of CYCLOFERONE was 129°–132° C.

CASE 2 276 grams of sodium 2-/acridone-9-on-10-yl/acetate were dissolved by stirring in 400 milliliters of distilled water. Concentrated hydrochloric acid was added to pH 3. The resulting precipitate was filtered, washed in 100 milliliters of distilled water, and re-filtered. The precipitate was recrystallized from dimethylformamide and water mixed at a ratio of 3:1. The 2-/acridone-9-on-10-yl-/acetic acid precipitate was dried for 3 hours at 105° C. before proceeding as indicated in Case 1. The process yield was 398 grams of 89% pure CYCLOFERONE with a melting point upon being recrystallized from low-grade alcohols of 129°–132° C.

CASE 3 282 grams of 2-ethyl-/acridone-9-on-10-yl/ acetate was suspended in 500 milliliters of 20% water sodium hydroxide. The suspension was brought to a boiling point and stirred while boiling until the precipitate completely dissolved. The reacting body was cooled to room temperature and concentrated hydrochloric acid was added to pH 3.0. The precipitate 2-/acridone-9-on-10-yl/acetic acid was filtered, washed in 300 ml water and re-filtered. Recrystallization was performed as described in Case 2 and the resulting 2-/acridone-9-on-10-yl/acetic acid was used in the steps described in Case 1.

The process yield was 381 grams of 86% pure CYCLOFERONE having upon recrystallization from lower-grade alcohols a melting point of 129°–132° C.

Physical/chemical characteristics of cycloferone are shown in Table 1 below. CYCLOFERONE exerts no mutagenic, teratogenic, embryotoxic, or allergenic effects.

prototype compound 10-carboxymethyl-9-acridone dimethylamino-ethyl ether chlorhydrate described in Polish Patent No. 139805 of Jul. 31, 1987.

TABLE 2

| Compound Parameter | Administration Mode | $LD_{50}$ |
|---|---|---|
| CYCLOFERONE | Intravenous | 400 |
|  | Intramuscular | 500 |
| 10-carboxymethyl-9-acridone | Intravenous | 400 |
| dimethylamino-ethyl ether chlorhydrate | Intramuscular | 600 |

As can be seen from the data in the table, CYCLOFERONE and the prototype compound are low-toxicity substances upon parenteral application.

CASE B Interferonogenic Activity

The ability of low-molecular fluorenone-thylorone class compounds to induce generation of interferon is universally known. See N. P. Chizhov, F. I. Ershov, and M. K. Indulen, "Fundamentals of Experimental Chemical Therapy for Viral Infections," Riga: 89 (1988). The interferon-induction effect is also exerted by low-molecular weight acridanone-class compounds, for example, 10-carboxymethyl-9-acridone dimethylaminoethyl ether chlorhydrate. See Polish Patent No. 139805 of Jul. 31, 1987.

TABLE 1

| Parameter | | Analytical Data |
|---|---|---|
| Appearance | | Crystalline powder of yellow color, odorless |
| Solubility | | Readily soluble in water; poorly soluble in lower-grade alcohols; and insoluble in ether, chloroform, and acetone |
| UV-spectrum (nm) (0.002% solution in water) | | 210, 255, 392, 408 |
| PMR-spectrum ($\delta$) (in $D_2O$) | | 2.5 (s), 3.0–3.1 (t), 3.5–3.8 (m), 4.0 (m), 4.5 (s), 7.1–7.25 (m), 7.55–7.65 (m), 7.95–8.05 (m) |
| NMR$^{13}$C-spectrum ($\delta$) (in $D_2O$) | | 35.622; 50.472; 51.761; 63.352; 68.710; 71.185; 71.391; 71.594; 115.829; 121.065; 122.686; 126.844; 135.550; 175.602; 179.532 |
| Elemental analysis (%) | | |
| $C_{22}H_{26}N_2O_8$ | Calculated C | 58.74 |
| | H | 5.83 |
| | N | 6.73 |
| | Actual C | 58.52 |
| | H | 5.64 |
| | N | 6.81 |
| Molecular mass | | 446.25 |
| Melting temperature (°C.) | | 129–132° C. |

EXAMPLE 2

Best Mode of Carrying Out the Invention

Therapeutic and biological characteristics of CYCLOFERONE were investigated in experiments in animals. CYCLOFERONE exhibited a broad range of biological activities, low toxicity, good endurance characteristics, and high therapeutic-efficiency.

CASE A Acute toxicity of CYCLOFERONE was studied in ristal-strain mongrel white mice weighing 18–20 grams. Intravenous and intramuscular injections were given of 2000 mg/kg and less in two stages. The follow-up period was 14 days. The lethal dose (LD50) was calculated by the Kerber technique. Results of the acute toxicity studies are shown in Table 2 below wherein CYCLOFERONE is compared to a The interferon-inducing activity of CYCLOFERONE was studied in mice and in animal and human cell cultures. BALB mice weighing 10–12 grams were given single hypodermic injections of 200 mg/kg cycloferone or 50 mg/kg thylorone. At predetermined time intervals interferon titers were measured in the blood by conventional techniques on homologous cells ($\alpha$-929) grown in 96-well plates in a $CO_2$-containing incubator. The test-virus was the encephalomyocarditis virus. Comparison data of interferon-inducing activity exhibited by CYCLOFERONE, thylorone, and the CYCLOFERONE structural prototype 10-carboxymethyl-9-acridone dimethylaminoethyl ether chlorhydrate are shown in Table 3, wherein interferon titers are presented as international units/milliliter.

TABLE 3

| Preparation | Dose (mg/kg) | Interferon titers (IU/ml) on Administration (Hour) | | | | | | |
|---|---|---|---|---|---|---|---|---|
| | | 1 | 2 | 4 | 8 | 18 | 24 | 48 |
| Cycloferone | 200 | 80 | 160000 | 640800 | 8000 | 640 | 320 | 10 |
| Thylorone | 50 | <40 | <40 | <40 | 40 | 640 | 20 | <10 |
| Dimethylamino-ehtyl ether chlorhydrate 10-carboxymethyl--9-acridone | 400–600 | — | 100 | 1000 | — | — | — | — |

As can be seen from the data presented, CYCLOFERONE induces production of high titers of interferon 2–8 hours after administration. The peak of interferon production in the case of CYCLOFERONE exceeds interferon levels in circulation in mice in response to thylorone injection by 1000 times and in response to the prototype by 640 times.

The superior interferon-inducing effect of CYCLOFERONE has also been shown in cell culture. Splenic- and peripheral-blood lymphocytes were isolated from BALB mice and treated with cycloferone or thylorone. The initial concentration was $5 \times 10^6$ cells/milliliter. The dynamics of interferon accumulation were studied in the cultural fluid of the lymphocytes grown on plastic plates in the presence of $CO_2$. Interferon titers in splenocytes and blood cells on administration of CYCLOFERONE or thylorone are shown in Table 4.

TABLE 4

| Cells | Cycloferone | | | | | | Thylorone | | | | | |
|---|---|---|---|---|---|---|---|---|---|---|---|---|
| | 24 hr | 48 hr | 72 hr | 96 hr | 120 hr | 144 hr | 24 hr | 48 hr | 72 hr | 96 hr | 120 hr | 144 hr |
| Splenocytes | 2560 | 1280 | 5120 | 640 | 80 | <10 | 15 | 30 | 640 | 320 | 15 | <5 |
| Peripheral-blood lymphocytes | 2560 | 280 | 2560 | 160 | <10 | <10 | 40 | 80 | 320 | 80 | 10 | <10 |
| T-lymphocytes | 10 | 40 | <10 | <10 | <10 | <10 | 15 | 60 | 5000 | 3600 | 960 | 5 |
| B-lymphocytes | 2500 | 1280 | 5120 | 1280 | 160 | 10 | 15 | 30 | 320 | <10 | <10 | 5 |

The results presented in Table 4 indicate that cycloferone induces significantly higher interferon levels in a mixed splenic peripheral-blood lymphocyte culture than does thylorone.

Supporting evidence has also been found for the interferonogenic activity of CYCLOFERONE in human blood culture. For this purpose, human peripheral-blood lymphocytes were obtained by separating donor blood. The lymphocyte concentration was $2 \times 10^6$ cells/milliliter. The cells were grown in 24-well plastic plates. Lymphocyte induction was performed with CYCLOFERONE and thylorone at concentrations of 600 and 200 milligrams/milliliter, respectively. Interferon levels in the culture fluid was evaluated by titration on diploid human cells (M-19). The test virus utilized was vesicular stomatitis. Interferon specimens were neutralized with conventional α-9 and β-9 human interferon antisera with international human interferon standards used for reference.

Results of interferon induction in human lymphocytes are shown in Table 5.

TABLE 5

| Preparation | Interferon Titers (U/ml) | | | | |
|---|---|---|---|---|---|
| | 24 hr | 48 hr | 72 hr | 96 hr | 120 hr |
| Cycloferone | 1280 | 40 | 80 | <10 | <10 |
| Thylorone | 15 | 60 | 120 | 30 | <15 |

As indicated in Table 5, cycloferone induces interferon production in human peripheral-blood lymphocyte cultures at a rate 90 times higher than thylorone.

CASE C CYCLOFERONE Anti-viral Activity

CASE 1C High anti-viral activity of CYCLOFERONE was demonstrated in experimental mice injected with vernal encephalitis virus (VE).

At present only inactivated vaccines of low effectiveness which require annual vaccinations due to rapidly decreasing resistance are used in treatment of vernal encephalitis. No other treatments are available in medical practice. See Smorodintsev A. A. and Dubov A. V., "Vernal encephalitis and preventive vaccination," M., (1986).

To estimate cycloferone effectiveness against VE, the ABSETTAROV strain of VE virus was used. The virus titer in intracerebral infection was 7.0–8.0 lg $LD_{50}$ and in subcutaneous infection was 5.0 lg $LD_{50}$. The experiment was performed on non-line white mice weighing 12–14 grams by hypodermic injection of VE virus.

CYCLOFERONE was dissolved in salt solution, and hypodermic injections were given to a test group. The controls had hypodermic injections of salt solution. The follow-up period was 21 days. The criteria for cycloferone effectiveness were survival and average life of the test mice, as compared to the control mice. Results of the experimental studies are presented in Table 6.

TABLE 6

| Administration Schedule and Dose | Animal Group | Animals Infected | Mortality Number | % | Effectiveness Index (EI*, %) | Average Survival (Days) | Reduction Multiple for Mortality (RM**) |
|---|---|---|---|---|---|---|---|
| 4 hours before infection (200 mg/kg) | Test | 306 | 11 | 3.6 | 95 | 11.8 | 22.5 |
| | Control | 300 | 243 | 81.0 | — | 9.4 | — |
| 4 hours after infection (200 mg/kg) | Test | 20 | 7 | 35.0 | 44 | 11.0 | 1.8 |
| | Control | 20 | 13 | 65.0 | — | 9.8 | — |

EI* — compound's therapeutic effectiveness index is calculated according to formula:

$$EI^* = \frac{\text{control group protection multiple} - 1}{\text{test group protection multiple}} \times 100$$

RM** — Reduction multiple for lost mice in test group as compared to controls is calculated according to the formula:

$$RM^{**} = \frac{\text{\% mortality in control group}}{\text{\% mortality in test group}}$$

The data support distinct protective effects of the CYCLOFERONE preparation. Additionally, special examinations indicated that no VE virus was evident in the brain of the mice injected with CYCLOFERONE four and seven days after injections, while in the brain of control mice the virus reproduced in high titers.

CASE 2C CYCLOFERONE activity has been demonstrated against the human immunodeficiency virus (HIV). Only one medication has been permitted to date for use in AIDS treatment. This is a nucleoside-based azidothymidine (retrovir, zidovudine) with which significant disadvantages are associated such as high toxicity and rapid mutation of the virus. Moreover, the medication cannot guarantee survival, only prolongation of life. See Chizhov N. P., *Antibiotiki i khimioterapiia*, 36(4): 38–41 (1991).

To evaluate CYCLOFERONE effectiveness against HIV reproduction, line U-937 monocyte-cell culture was employed. The cells were grown at the Russian Medical University (RMU) in tube medium—1640 containing 20% calf foetal serum at end concentration of $0.5$–$0.7 \times 10^6$ cells/ml. Prior to introducing CYCLOFERONE in the supporting medium, the cellular suspension was injected with a culture-fluid concentrate, containing HIV produced by HTA-41 cell lines. The cells were then incubated for 3–4 days at 37° C. with subsequent replacement of nutrient medium. On the fifth and seventh day after infection, the presence of virus-specific antigen was established through indirect immunofluorescence assay using anti-HIV antibodies.

Results of the evaluation of the inhibiting effect of CYCLOFERONE on HIV-antigen expression in HIV-inducing U-937 monocytic cells, as compared to results for azidothymidine (obtained from Wellcome, Inc., Great Britain), are shown in Table 7.

TABLE 7

| Preparation | Concentration (mg/ml) | Number of cell containing HIV antigen by IIFR* (%) | |
|---|---|---|---|
| | | Day 5 | Day 7 |
| CYCLOFERONE | $0.09 \times 10^{-3}$ | 5.1 | 4.8 |
| | $0.18 \times 10^{-3}$ | 2.1 | 3.7 |
| Azidothymidine | 0.08 | 6.5 | 4.7 |
| | 0.16 | 3.9 | 2.4 |
| Controls | — | 35.6 | 32.4 |

*IIFR - indirect immunofluorescence reaction

CYCLOFERONE exerts the same effect on HIV-antigen expression in monocytic cell culture at almost 1000-times lower concentrations than azidothymidine.

CASE D The anti-parasitic activity of CYCLOFERONE was studied in an experimental chlamydia model in comparison to tetracycline hydrochloride, the traditional medication for this human zymotic pathology. See M. D. Mashkovskii, "Lekarstvennye sredstva," p. 221 in *Meditsina*, Part 2 (1987). Induction of interferon has not previously applied in the treatment of chlamydia infections. The application of tetracycline-series antibiotics against chlamydia infections requires a prolonged course of treatment and is hampered by their toxicity and rapid growth of resistant pathogen forms.

Experiments were performed involving *C trachomatis* infection of non-line whim mice weighing 16–18 grams. In test groups, CYCLOFERONE was administered 24 hours after infection at a dose of 60 mg/kg or was administered twice, once 24 hours after infection and once at a 96-hour interval. Alternatively, a single tetracycline hydrochloride injection (100 mg/kg) was administered on conventional schedule for 5 days. Controls had salt-solution injections.

Therapeutic effectiveness was evaluated by cytoscopic examination of stained smears from lymph nodes and the lung for pathogenic multiplication. Results of the outcome of CYCLOFERONE and tetracycline treatment for chlamydia are compared in Table 8.

TABLE 8

| Preparation | Administration Schedule | Dose (mg/kg) | Effectiveness Index | | | |
|---|---|---|---|---|---|---|
| | | | Lymph nodes | | Lung | |
| | | | 3 days | 7 days | 3 days | 7 days |
| CYCLO-FERONE | 24 hours after infection | 60 | 4.7 | 1.8 | 3.6 | 3.2 |
| | 24 and 96 hours after infection | 60 | 4.4 | 2.6 | 3.4 | 3.9 |
| Tetracycline hydrochloride | Daily for 5 days | 100 | 0.9 | 0.6 | 1.8 | 1.0 |

Comparisons of the results obtained indicate a more clearly defined therapeutic effect of CYCLOFERONE the effectiveness index being 2–4 times higher than in the tetracycline-treated animal group.

CASE E Anti-promotive Activity

Cancerogenesis is known to be a multi-stage process involving initiation, promotion, and progression. The first two stages involve development of primary neoplasms, while progression involves further growth of neoplasms. Substances exhibiting anti-promotive activity can be regarded as potential anti-cancer agents.

Studies were performed on female BALB/c mice weighing 25.0 grams. CYCLOFERONE was compared to a fluorenone-class thylorone-synthesis preparation.

The compounds were administered daily for 6 days in optimal doses. Controls were given physiological solution. Six hours after the last injection the animals were sacrificed. Sections of the lung and liver were cut out, submerged in 199 medium, and cellular cohesion was measured. Measurements were performed with a micro-manipulator by modified Kuman technique. See Modianova E. A., *Voprosy onkologii*, 19(6): 83–88 (1973).

For each experimental point, cellular cohesion was measured in 4–5 mice. One tissue segment from each of the mice measuring 10–30 cells was examined. Results from the analysis of anti-promotive activity are shown in Tables 9 and 10.

TABLE 9

| Compound | Administration Mode (Dose, mg/kg) | Hepatocytic Cohesion (mg/1 cell) | P |
|---|---|---|---|
| CYCLOFERONE | Intraperitoneal (100.0) | 0.113 ± 0.017 | <0.05 |
| Thylorone | Intraperitoneal (10.0) | 0.053 ± 0.008 | >0.05 |
|  | Oral (200.0) | 0.076 ± 0.013 | >0.05 |
| Controls | Physiological | 0.056 ± 0.008 | — |

Upon CYCLOFERONE administration cohesion in hepacytes increases twofold, while thylorone indices are the same as in the controls.

TABLE 10

| Preparation | Administration Schedule (Dose, mg/kg) | Cellular Cohesion in Lung Alveoli (mg/kg) | P |
|---|---|---|---|
| Cycloferone | Intraperitoneal (100.0) | 0.324 ± 0.033* | <0.05 |
| Thylorone | Intraperitoneal (10.0) | 0.289 ± 0.028 | >0.05 |
|  | Oral (200.0) | 0.290 ± 0.024 | >0.05 |
| Controls | Physiological solution | 0.279 ± 0.024 | — |

*reliable differences

As is demonstrated by the data in Table 10, CYCLOFERONE increases cellular cohesion in lung alveoli 1.2 times in comparison to thylorone and the controls.

Studies of the anti-promotive activity of CYCLOFERONE indicate that it behaves as a classical adhesion factor, doubling cellular cohesion in the liver and increasing cohesion 1.5 times in the lung alveoli. See Modianova E. A., et al., *Problemy Experimental'nojo Kantscrogeneza*, (Problems of Experimental Cancerogenesis), 51: 135–139 (1983).

CASE F Radioprotective Activity

The radioprotective activity of CYCLOFERONE was studied in BALB/c mice weighing an average of 26.7±1.84 grams. The mice were exposed to $^{60}$Co irradiation in the range of 7.5+9.0 Grey. CYCLOFERONE was administered in a single dose of 300 milligram/kilogram by hypodermic injection 2 hours before irradiations. Controls were given physiological solution injections. The follow-up period was 14 days.

Effectiveness criteria were based on survival data. Findings from the experimental studies are presented in Table 11 below.

TABLE 11

| Protection Preparation | Irradiation Dose (GR) | Number of animals | | Mortality | |
|---|---|---|---|---|---|
| | | Total | Deaths | (%) | (%) |
| CYCLOFERONE | 8.0 | 10 | 1 | 10 | 60 |
| | 8.5 | 10 | 3 | 30 | 50 |
| | 8.7 | 10 | 1 | 10 | 70 |
| | 9.0 | 10 | 6 | 60 | 40 |
| | 9.3 | 10 | 9 | 90 | 10 |
| | 10.0 | 10 | 10 | 100 | 0 |
| Phys. Solution | 7.5 | 10 | 4 | 40 | — |
| | 7.8 | 10 | 3 | 30 | — |
| | 8.2 | 10 | 7 | 70 | — |
| | 8.5 | 10 | 8 | 80 | — |
| | 8.7 | 10 | 8 | 80 | — |
| | 9.0 | 10 | 10 | 100 | — |
| | 9.3 | 10 | 10 | 100 | — |
| | 10.0 | 10 | 10 | 100 | — |

Thus, single subcutaneous administrations of CYCLOFERONE two hours before exposure protected 70% of mice against $^{60}$Co of 8.7 Gy, 50–60% of mice against 8.0–8.5 Gy, and 40% of mice against the maximum dose of 9.0 Gy, testifying to the high radioprotective effects of CYCLOFERONE.

The foregoing examples indicate that the inventors succeeded in manufacturing a new acridone-class compound featuring a wide range of biological activities including those previously unknown (anti-parasitic and radioprotective) for the compound class.

We claim:

1. An acridanone derivative which is N-methyl-N-α-D-glucopyranosil-ammonium-2-acridone-9-on-10-yl-acetate, characterized by the formula

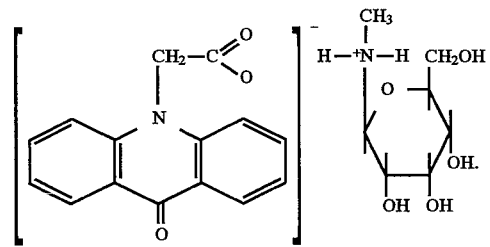

2. A pharmaceutical composition comprising the acridanone derivative of claim 1 in conjunction with a pharmaceutically acceptable diluent, adjuvant or carrier.

3. A method of treating a subject suffering from a *chlamydia trachomatis* infection comprising administering to said subject an effective amount of the acridanone derivative of claim 1.

* * * * *

UNITED STATES PATENT AND TRADEMARK OFFICE
CERTIFICATE OF CORRECTION

PATENT NO. : 5,658,886
DATED : August 19, 1997
INVENTOR(S) : Chizhov, N.P. *et al.*

It is certified that error appears in the above-identified patent and that said Letters Patent is hereby corrected as shown below:

Title page, Abstract, line 6, "...anti-vital..." should be --anti-viral--.

Col. 8, line 28, "...whim mice..." should be --white mice--.

Signed and Sealed this

Third Day of February, 1998

*Attest:*

BRUCE LEHMAN

*Attesting Officer*  *Commissioner of Patents and Trademarks*